United States Patent [19]

Jaffe

[11] Patent Number: 5,518,886
[45] Date of Patent: May 21, 1996

US005518886A

[54] BLOOD LEAD DIAGNOSTIC ASSAY

[75] Inventor: Eileen K. Jaffe, Jenkintown, Pa.

[73] Assignee: Fox Chase Cancer Center, Philadelphia, Pa.

[21] Appl. No.: 100,980

[22] Filed: Aug. 3, 1993

[51] Int. Cl.$^6$ .................. G01N 33/536; G01N 33/543; G01N 33/573

[52] U.S. Cl. .................. 435/7.1; 435/7.4; 435/183; 436/536; 436/518; 436/77; 436/177

[58] Field of Search .................. 435/4, 232, 183, 435/7.1, 7.4, 815; 436/518, 536, 77, 177

[56] References Cited

U.S. PATENT DOCUMENTS

| | | | |
|---|---|---|---|
| 3,652,761 | 3/1972 | Weetall et al. | 435/7.4 |
| 4,876,191 | 10/1989 | Hollander et al. | 435/7.4 |

FOREIGN PATENT DOCUMENTS

WO93/01310  1/1993  WIPO.

OTHER PUBLICATIONS

S. K. Cummins et al., Pediatrics, 90: 995–997 (1992).
B. E. Jacobson et al., Clin. Chem., 37: 515–519 (1991).
M. R. DeBaun et al., Pediatrics, 88: 121–131 (1991).
M. D. McElvaine et al., J. Pediatrics, 119: 548–550 (1991).
A. Berlin et al., Z. Klin. Chem. Klin. Biochem., 12: 389–390 (1974).
E. K. Jaffe et al., Biol. Trace Elem. Res., 28: 223–231 (1991).
R. Taylor, J. NIH Res., 2: 57–60 (1990).
K. Tomokuni et al., Toxicol. Letters, 59: 169–173 (1991).
H. Monteiro et al., Arch. Biochem. Biophys, 271: 206–216 (1989).
J. L. Granick et al., Biochem. Med., 8: 149–159 (1973).
P. Gibbs et al., Biochem. J., 230: 25–34 (1985).
H. Fujita et al., Biochim. Biophys. Acta, 678: 39–50 (1981).
A. –L. Wang et al., Hum. Genet., 70: 6–10 (1985).
L. J. Van Eldick et al., Meth. Enzymol., 139: 393–405 (1987).
G. Battistuzzi et al., Ann. Hum. Genet., 45: 223–229 (1981).
R. Petrucci et al., Hum. Genet., 60: 289–290 (1982).
D. F. Bishop et al., Meth. Enzymol., 123: 339–345 (1986).
Chakrabarti, S. K.; Brodeur, J.; Tardif, R. Fluorometric determination of S–Amino laevulinate dehydratase activity in human erythrocytes as an index to lead exposure. Clin. Chem. 21(12) 1783–1787, 1975.
Fujita, H; Yamamoto, R.; Sato, K.; and Ikeda, M. In vivo regulation of δ–aminolevulinate dehydratase activity. Toxicology and Applied Pharmacology 77:67–75, 1985.
Mitchell, R. A.; Drake, J. E.; Wittlin, L. A.; and Rejent, T. A. Erythrocyteporphobilino–gin synthase (delta–aminolaevulinate dehydratase) activity: A reliable and quantitative indicator of lead exposure in humans. Clin. Chem. 23(1) 105–111, 1977.
Sakai, T.; Yanagihara, S.; and Ushio, K. Restoration of lead–inhibited 5–aminolevulinate dehydratase activity in whole blood by heat, zinc ion, and (or) dithiothreitol. Clin. Chem. 26 (5) 625–628, 1980.

*Primary Examiner*—James C. Housel
*Assistant Examiner*—Nancy J. Parsons
*Attorney, Agent, or Firm*—Dann, Dorfman, Herrell and Skillman

[57] ABSTRACT

Diagnostic blood lead assays using porphobilinogen synthase protein function as an indicator of physiological response to lead exposure and as an indicator of the time period of lead exposure are disclosed.

12 Claims, No Drawings

BLOOD LEAD DIAGNOSTIC ASSAY

FIELD OF THE INVENTION

The present invention relates to an assay for assessing the severity of the physiological response to lead exposure. The assay of the invention provides a rapid, sensitive and reliable way of determining lead concentrations in biological samples.

BACKGROUND OF THE INVENTION

Description of the Prior Art

Measurement of the severity of physiological response to lead exposure is important for the public health goals of treatment and prevention of lead poisoning. Lead has long been known as a potent neurotoxin which can cause developmental disabilities, behavioral disturbances and mental retardation in children. In adults, the symptoms of plumbism often resemble schizophrenia. Lead poisoning in children and adults is curable, although the neurological damage in children is irreversible.

Sources of lead include lead-based paint or lead solder in pipes, airborne lead from automobile and industrial emissions and lead from occupational sources. Lead can be ingested through the lungs or digestive tract and once ingested, lead accumulates in bones and teeth. Long-term chelation therapy can be used to remove lead from bone tissue. However, if lead poisoning is untreated, the sequestered lead in bone tissue can be reintroduced into the blood stream during periods of bone resorption such as osteoporosis, pregnancy and lactation. In the latter two periods, lead is presented as an irreversible neurotoxin to the fetus and infant. For those reasons, early detection and prevention of lead exposure is essential, especially for small children.

The Centers for Disease Control (CDC) in Atlanta, Ga. have established a guideline which consists of a threshold level of blood lead at which medical intervention is required. The CDC recently lowered the guideline from $\geq 25$ ug/dL to $\geq 10$ ug/dL in response to scientific evidence that neurotoxicity in children and infants can occur at very low levels of lead exposure. The CDC has also recommended routine screening of all children for exposure to lead (Preventing lead poisoning in young children: A statement by the Centers for Disease Control—October 1991. Atlanta, Ga.: Centers for Disease Control; 1991.; S. K. Cummins and L. R. Goldman, Pediatrics 90:995–997 (1992)). With the exception of atomic absorption spectroscopy, current diagnostic methods for measuring blood lead are not sufficiently sensitive, reliable or accurate to routinely measure such low levels of blood lead. In addition, the present methods, including atomic absorption spectroscopy, suffer from limitations of expense and time-consuming procedures.

Atomic absorption spectrometry, for example, is a sensitive and accurate method for quantitating blood lead concentration. This method can be used to measure blood lead concentrations below 10 ug/dL; however, atomic absorption spectrometry requires expensive instrumentation and high levels of technical expertise, and therefore cannot be performed in the field (B. E. Jacobson, G. Lockitch, and G. Quigley, Clin. Chem. 37:815–519 (1991)). Additional disadvantages of this method include high expense per test and a time delay between sampling and acquisition of test results. Due to the expense involved and instrumentation required, atomic absorption spectroscopy is not optimal for use as a routine screening assay for field use.

Another method for measuring blood lead concentration is the Erythrocyte Protoporphyrin (EP) test (also known as the Zinc Protoporphyrin test) which is based on the proportional increase in concentration of erythrocyte protoporphyrin in response to lead exposure. Erythrocyte protoporphyrin is a precursor of heme that accumulates as a result of high lead levels interfering with normal heme synthesis. At blood lead concentrations $\geq 40$ ug/dL, the concentration of erythrocyte protoporphyrin increases exponentially, therefore an erythrocyte protoporphyrin concentration above a specified threshold provides an indication of excessive lead exposure (M. R. DeBaun and H. C. Sox, Jr., Pediatrics, 88:121–131 (1991)). Low sensitivity is the main disadvantage of the EP method; the test is not sensitive to blood lead concentrations below 25 ug/dL (M. D. McElvaine, H. G. Orgach, S. Binder, L. A. Blanksma, E. F. Maes and R. M. Krieg, J. Pediatrics 119:548–550 (1991)). Although inexpensive and easy to perform, the EP test is not a good screening assay because its sensitivity does not allow measurement of the low blood lead levels that the CDC has targeted.

The European Standardized Method (ESM) of determining blood lead concentrations is based on lead inhibition of the enzyme activity of porphobilinogen synthase (PBGS) (also known as delta-aminolevulinic acid dehydratose) (A. Berlin and K. M. Schaller, J. Clin. Chem. Clin. Biochem. 12:389–380 (1977)). PBGS catalyzes the asymmetric condensation of two molecules of 5-aminolevulinic acid (ALA) to form porphobilinogen (PBG) and is extremely sensitive to the presence of divalent lead. The inhibitory effect of lead on PBGS is well established and PBGS has been identified as the most sensitive early indicator of lead poisoning in humans (E. K. Jaffe, S. Bagla and P. A. Michini, Biol. Trace Elem. Res. 28:223–231 (1991)). Inhibition of PBGS by lead causes accumulation of ALA which is believed to be responsible for the neurologic damage in individuals exposed to lead and contributes to the anemia associated with lead poisoning (R. Taylor, J. NIH Res. 2:57–60 (1990); K. Tomokuni, M. Ichiba and Y. Hirai, Toxicol. Lett. 59:169–173 (1991); H. P. Monteiro, D. S. P. Abdalla, O. Augusto and E. J. H. Bechara, Arch. Biochem. Biophys. 271:206–216 (1989)).

The European Standard Method is based on measurement and comparison of PBGS enzyme activity as inhibited by lead and PBGS enzyme activity as reactivated by heat and dithiothreitol (T. Sakai, S. Yanagihara and K. Ushio, Clin. Chem. 26:625–628 (1980)). The ratio of inhibited PBGS activity to reactivated PBGS activity is directly proportional to the blood lead concentration (J. L. Granick, S. Sassa, S. Granick. R. D. Levere and A. Kappas, Biochem. Med. 8:149–159 (1973); R. A. Mitchell, J. E. Drake, L. A. Wittlin and T. A. Rejent, Clin. Chem. 23:105–111 (1977)). The analysis of PBGS activity is based on colorimetric determination of the enzyme product, PBG, through reaction with Ehrlich's reagent. ESM is sensitive to low blood lead concentrations; however, the main disadvantage of the ESM is its irreproducibility caused by factors such as pH, temperature, buffer, variable metal contamination and concentrations of other blood proteins (E. K. Jaffe, S. Bagla and P. A. Michini, Biol. Trace Elem. Res. 28:223–231 (1991) and references therein). In addition, the ESM assay time is long (approximately ninety minutes) and because the assay requires chemical laboratory equipment, the test cannot be easily performed in the field. Although sensitive and inexpensive, the ESM assay is not a good screening method for low blood lead concentrations because it is not considered a reliable method for assessing lead exposure.

The assay described in the International Patent application PCT/US92/05658, entitled "Lead Assays", involves use of PBGS as a biodetector molecule to measure lead concentrations in biological as well as nonbiological materials. For this assay, PBGS can be isolated from tissue or purchased commercially. In carrying out this assay, nitric acid is used to extract elemental lead from any sample. The lead concentration of the sample is then determined either by measuring the PBGS activity after exposure to the sample or by measuring the amount of PBGS complexed to lead after exposure to the sample.

In the assay described in PCT/US92/05658, PBGS activity is measured by monitoring the product PBG formed or the substrate ALA consumed using either chemical labelling of or antibody binding to the product or substrate. Alternatively, the amount of PBGS bound to lead is measured using antibodies that bind specifically to different forms of the PBGS-lead complex. A purported advantage of using PBGS as a biological detector is the ability to test any solution for lead content. However, an apparent disadvantage of this method as a screening test for human blood is the lack of specificity to the human subject since PBGS from any species can be used.

The essential criteria for a useful screening and measuring method for lead exposure in blood are specificity for lead and sensitivity for physiological responses to lead exposure at concentrations of current concern, i.e. the CDC guideline which defines an elevated blood lead concentration as $\geq 10$ ug/dL. Additional criteria for a routine screening assay include reliability, ease of performance, low cost, speed, small sample size and the capacity for use in clinical or field settings.

SUMMARY OF THE INVENTION

In accordance with the present invention, there is provided a method for determining the severity of a subject's physiological response to lead exposure. The method is based on the inhibitory effect of lead on the protein function of PBGS, a protein found in certain biological fluids. The method involves isolating PBGS from a sample of the biological fluid, preferably blood, and measuring the lead inhibition of PBGS protein function. The degree of inhibition of PBGS protein function indicates the severity of the subject's physiological response to lead exposure.

The method of the invention uses the subject's own PBGS as a biological marker to determine the subject's physiological response to lead exposure. The present invention includes the step of isolating PBGS from the sample, thereby removing the confounding effect of interfering substances in the sample composition. The use of PBGS as a biological marker is an additional advantage of this assay method over prior art methodology because the PBGS is specific to the subject and will reflect individual variations in PBGS activity. The assay method described herein is sensitive to the low blood lead concentration that the CDC has targeted as the threshold for medical intervention and it also advantageously uses a much shorter assay time than existing methods. Another advantage of this invention is that it provides an estimate of the relative time period of lead exposure by comparing the total amount of PBGS present in the sample to the amount of PBGS inhibited by lead. The method is adaptable to a manual dipstick format or an automated clinical analyzer format and therefore can be used in field or clinical settings.

In summary, the present invention overcomes the disadvantages of the prior art by providing a sensitive, reliable, quick, easy to perform and portable method for assaying the severity of the subject's physiological response to lead exposure.

DETAILED DESCRIPTION OF THE INVENTION

As used herein, the term "protein function" refers to enzyme activity and antibody binding, as well as structural, hormonal or product-binding functions. Furthermore, the expression "substantially regain protein function" as used herein refers to the appreciable recovery of PBGS activity from the effects of lead inhibition over time as the inhibiting lead is replaced by zinc through competitive binding. In the case of enzyme activity, for example, a twofold or greater recovery, as compared with activity as measured promptly upon isolation of PBGS, is considered to be substantial.

The assay of the invention essentially involves two steps, i.e., isolation of PBGS and measurement of PBGS protein function as inhibited by lead. Antibodies are the most sensitive and specific means of separating a specific protein from a complex biological matrix, such as blood. A relatively normal dissociation constant for an antibody-antigen complex is $10^{-11}M$. Since the concentration of PBGS is approximately $10^{-7}M$ in whole human blood and $10^{-8}M$ in hemolysate (P. N. B. Gibbs, A-G. Chaudhry and P. M. Jordan, Biochem. J. 230:25–34 (1985)), PBGS can be quantitatively removed from a hemolysate sample using monoclonal or polyclonal antibodies. PBGS can be isolated from the blood of a test subject using antibodies that bind specifically to any form of PBGS including the active and inhibited forms as well as different alleles of the protein. As used herein, the term "subject" includes both humans and animals.

Polyclonal antibodies to PBGS can be made with the purified protein using methods known in the art. Antibodies are raised in suitable animals such as mice, rabbits, sheep, goats or horses by injecting repeatedly with the PBGS antigen in the presence or absence of adjuvents as appropriate. The sera containing the PBGS-specific antibodies are then collected and the specificity and titre of antibody response are tested using procedures known in the art.

Human PBGS for raising antibodies may be isolated from outdated blood by a method which uses a batch extraction technique to remove the hemoglobin (P. N. B. Gibbs, A-G. Chaudhry and P. M. Jordan, Biochem. J. 230:25–34 (1985)). This purification protocol allows the isolation of >100 mg of human PBGS from 7.5 liters of human blood. Human PBGS-specific antibodies can be raised in both goats (H. Fujita, Y. Orii and S. Sano, Biochim. Biophys. Acta 678:39–50 (1981)) and mice (A. L. Wang, K. H. Astrin, W. F. Anderson and R. J. Desnick, Hum. Genet. 70:6–10 (1985)); however, due to extensive identity between human and other species' PBGS, the immune response will require boosting to obtain a high titre using a specific human PBGS peptide. The peptide will be specific to human PBGS and distinct from goat or mouse PBGS. Although the sequence of goat PBGS is not available, the known PBGS sequences (human, bovine, mouse, rat, pea, spinach, moth (selaginella martensii), yeast, E. coli, B. subtilis, and methanogenis socialbilis) were compared to find the most variable portions of the protein which could be used to design a peptide for boosting the antibody response. The least well-conserved regions of the PBGS sequence of different species occur in the N-terminal thirty amino acids (residues 80–85, 95–108, 183–193, 235–240, 261–269) and the carboxy terminal region (residues 320–330). Of those regions, the N-terminal sequence from residues 18–20 is among the least conserved sequences in mammalian species. Therefore, the first peptide to boost the immune response should be based on that region. The peptide preferably contains at least fifteen amino acids and should also contain an N-terminal cysteine residue to facilitate linkage to a carrier protein such as ovalbumin or keyhole limpet hemocyanin. The peptide may be covalently linked to the carrier protein using N-succinimidyl 3-(2-pyridyldithio)proprionate or 2-aminothiolane according to methods known in the art (L. J. Van Eldick and T. J. Lukas, Meth. Enzymol. 139:393–399 (1987)). Both carrier proteins may be used in different animals so that cross-screening can be performed to ensure that antibodies against the carrier protein were not boosted. Antibodies from different animals may be screened for their ability to bind to human PBGS using Ouchterlony diffusion plates and ELISA tests.

PBGS is known to be heterogeneous and two autosomal dominant alleles have been characterized (V. A. McKusick, Mendelian inheritance in man. Catalogs of Autosomal Dominant, Autosomal Recessive, and X-linked Phenotypes, Ninth Edition, Johns Hopkins University Press (1990); B. Battistuzzi, R. Petrucci, L. Silvagni, F. R. Urbani and S. Caiola, Ann. Hum. Genet. 45:223–229 (1981); R. Petrucci, A. Leonardi and G. Battistuzzi, Hum. Genet. 60:289–290 (1982)). Inclusion of the less common allele would be ensured by raising polyclonal antibodies against outdated blood from a mixed urban population. Thus the isolation step of the present assay method will be sensitive for all alleles of PBGS and it will also reflect individual sensitivities to lead and PBGS activity.

The next step in the invention is the measuring step which is based on measuring the lead inhibition of PBGS protein function to provide an indication of the severity of physiological response to lead exposure. The measured amount of lead inhibition of protein function can be related, if desired, to a predetermined standard obtained using atomic absorption spectroscopy to determine lead concentration in the sample. The assay of the invention may be practiced in a mode which uses PBGS as a biomarker to measure the severity of physiological response to lead exposure. This mode measures the PBGS protein function of enzyme activity of samples from subjects suspected of exposure to lead.

The PBGS protein function of enzyme activity can be measured by monitoring the PBGS-catalyzed formation of product PBG using any number of immunological or chemical techniques. For example, PBGS enzyme activity could be measured by monitoring PBG formation using monoclonal or polyclonal antibodies that bind specifically to the product PBG. According to the proposed embodiment of the invention, formation of PBG will be monitored colorimetrically using p-dimethylaminobenzaldehyde (PMAB) or it will be monitored fluorometrically using a conversion to uroporphyrinogen I. The measuring step based on PBGS enzyme activity relies on the fact that lead-inhibited PBGS can be reactivated by heating with zinc and a reducing agent, such as dithiothreitol, both of which are available commercially. The PBGS enzyme activity will be measured both before and after reactivation. The ratio of the lead-inhibited enzyme activity to the reactivated enzyme activity serves generally as a measure of blood lead concentration and more specifically as a measure of the subject's physiological response to lead exposure.

The colorimetric test involves the reagent PMAB which is available commercially and which forms a brightly colored pink complex with PBG under the appropriate chemical conditions. The complex can be either visually detected and scaled relative to a grid or detected in the visible wavelength range using a spectrophotometer. Unlike prior methodology which used a relatively long reaction time of sixty minutes or more, the assay of the present invention preferably uses a much shorter reaction time, on the order of five to ten minutes. The shorter reaction time lessens attenuation of lead inhibition and thus increases assay sensitivity as compared to the prior methodology, e.g., the European Standard Method. The latter approach does not account for the fact that PBGS protein function is restored over time due to replacement of the inhibitory lead by zinc.

The fluorometric test uses enzymes in the heme biosynthetic pathway to couple formation of PBG with formation of uroporphyrinogen I, an intrinsically fluorescent molecule (D. F. Bishop and R. J. Desnick, Meth. Enzymol. 123:339–345 (1986)). The reagent necessary for this method is phorphobilinogen deaminase (PBGD) which can be purified from outdated blood (M. Doss, F. Laubenthal and M. Stoeppler, Int. Arch. Occup. Environ. Health 54:55–63 (1984)). Ring closure of the PBGD product, hydroxymethybilane, to uroporphyrinogen I is spontaneous. Again a relatively short reaction time will be used to prevent attenuation of the lead inhibition and thereby improve assay sensitivity, by taking into account that protein function is restored over time due to replacement of the inhibitory lead by zinc.

Comparison of the amount of reactivated PBGS to the ratio of lead-inhibited to reactivated PBGS enzyme activity will provide an indication of the time period of lead exposure for a given subject. Increases in blood PBGS concentration occur in response to lead exposure as the body tries to compensate for the inhibitory effect of lead on PBGS protein function. It is believed that increases in blood PBGS concentrations may be proportional to the time period of lead exposure.

In practice, the assay may be used as a first screening test which will be sensitive over a range of blood lead concentrations from 2–>50 ug/dL or as an enhanced sensitivity test which will be sensitive for the range of blood lead concentrations from 0.2–10 ug/dL. The first screening test may be able to quantify blood lead concentrations to approximately 500 ug/dL. The enhanced sensitivity test will require the use of bovine serum albumin or small chemical chelators to potentiate the inhibition of PBGS by lead in order to be accurate at low blood lead concentrations (E. K. Jaffe, S. Bagla and P. A. Michini, Biol. Trace Elem. Res. 28:223–231 (1991)).

The following examples are provided to describe in further detail the method for determining the severity of a subject's physiological response to lead exposure in accordance with the present invention. These examples are intended to illustrate and not to limit the invention.

EXAMPLES

The reagents and accessories to be used in practicing the method of the invention may be conveniently packaged in kit form. The test kits may be used at home, in a physician's office, or in a public health service screening program. The following steps would be involved in the use of such a test kit.

(a) A PBGS sample would be taken as follows:

A precise volume of blood would be drawn by fingerstick from a clean finger and deposited into a first vessel containing blood lysis medium and a double dipstick, e.g. a unitary plastic strip or rod severable into two substantially identical units on which are immobilized anti-human-PBGS antibodies. The vessel would be shaken gently for a prescribed time to ensure red blood cell lysis and PBGS immobilization onto the antibody.

(b) Lead-inhibited PBGS would be distinguished from active PBGS as follows:

The double dipstick would be removed from the first vessel, split in half, and each individual dipstick, labelled either A or B, would be placed in a second vessel containing either of two corresponding buffers, A or B. Buffer A would be a neutral pH buffer containing no added zinc or reducing agents; this buffer would not reactivate lead-inhibited PBGS. Buffer B would contain all components of Buffer A, as well as zinc at a prescribed level and a reducing agent, such as dithiothreitol. The function of Buffer B is to reactivate lead-inhibited PBGS.

Warming in the palm of the hand with gentle shaking would serve to reactivate any lead-inhibited PBGS immobilized on dipstick B. This step would also serve to rinse both dipsticks of non-PBGS blood proteins such as hemoglobin.

(c) The substrate, amino-levulinic acid, would then be introduced into the second vessel and the PBGS-catalyzed reaction would be allowed to proceed for a short period of time, approximately five minutes. Alternatively, the dipsticks could be removed to a third vessel containing, respectively, Buffer A plus ALA and Buffer B plus ALA.

(d) The product, porphobilinogen, would be detected as follows. Because the PBGS would be immobilized on the dipstick, the reaction of step (c) would occur at the dipstick, rather than throughout the solution. The dipstick could be composed of a material, such as DEAE cellulose which would absorb the negatively charged PBG thus concentrating the product on the dipstick as well.

The PBG would be detected by exposing both dipsticks to solution containing p-dimethylaminobenzaldehyde (PMAB) in a reaction medium which promotes complex formation between PMAB and PBG. The PMAB:PBG complex is a deep pink color with an absorbance maximum at 555 nm and would be easily quantified by visual observations. The detection step would preferably take place in yet another vessel. Depending on the reagent selected for purposes of detection, it may be conveniently incorporated into the dipstick itself.

(e) The color of the two dipsticks A and B would be rated against a chart of colors ranging from no pink (rated as 1) through deep pink (rated as 30).

The ratio of the score of dipstick B to dipstick A would be indicative of the extent of lead intoxication. A ratio of 2 or less would be considered normal. Higher ratios would indicate some amount of lead intoxication and would be expected to approximate blood lead values.

The absolute value of the score of dipstick B would be indicative of the level of total activatable PBGS activity in the blood. Extraordinarily high values would be indicative of long term exposure to lead which might be useful for monitoring subjects who are occupationally exposed to lead. Extraordinarily low values might suggest a genetic condition indicative of a higher than normal sensitivity to lead intoxication.

An alternate method for detecting the product PBG in step (d) would be monitoring the formation of uroporphyrinogen I in a reaction medium containing porphobilinogen deaminase (PBGD). Uroporphyrinogen I is a fluorescent molecule which could be quantified using fluorescence spectroscopy.

An alternate format for the assay would involve a multireagent three-layered, sandwich-type dipstick. The first outer layer would contain antibodies to immobilize PBGS. The intermediate layer would bind the product PBG. The other outer layer would contain reagents necessary for detection of the product PBG. The reagents present in each layer would be activated sequentially as the dipstick is exposed to the different solutions.

An alternate format for the assay would involve carrying out the isolation and measuring steps of the assay using an automated clinical analyzer of the type which also performs other analyses on blood and/or urine.

While certain preferred embodiments of the present invention have been described and exemplified above, it is not intended to limit the invention to such embodiments, but various modifications may be made thereto, without departing from the scope and spirit of the present invention as set forth in the following claims.

What is claimed is:

1. A method for determining the severity of a subject's physiological response to lead exposure, based on the inhibitory effect caused by said lead on protein function of porphobilinogen synthase (PBGS) present in a biological fluid of said subject, said method comprising the steps of:

a) providing a test sample of said biological fluid;
   b) immunochemically isolating any said PBGS from said test sample and removing interfering substances from said isolated PBGS, said isolation step comprising complex formation between said PBGS and antibodies that bind specifically to said PBGS, whereby substantially all of said PBGS is isolated from said test sample;
   c) measuring the amount of lead inhibition of protein function of said isolated PBGS, the amount of inhibition of said protein function of said isolated PBGS being indicative of the severity of said subject's physiological response to the amount of lead to which said subject has been exposed.

2. A method as claimed in claim 1, which further includes the step of relating the measured amount of lead inhibition of protein function to a predetermined lead concentration standard to determine the concentration of said lead in said sample.

3. A method as claimed in claim 1, wherein the time period for performing said measuring step does not exceed that required for said isolated protein to substantially regain said protein function.

4. A method as claimed in claim 1, wherein said biological fluid is blood.

5. A method as claimed in claim 1, wherein the alleles of PBGS present in said test sample are isolated by complex formation with said alleles and polyclonal antibodies raised against outdated blood from a mixed urban population.

6. A method as claimed in claim 1, wherein said measuring step comprises measuring the protein function of enzyme activity of said PBGS as isolated, to provide a first activity measurement; reactivating any lead-inhibited PBGS present in said isolated PBGS; and measuring the protein function of enzyme activity of said PBGS as reactivated, to provide a second activity measurement, the ratio of the value obtained from said first activity measurement to the value obtained from said second activity measurement being indicative of the severity of said subject's physiological response to the amount of lead to which said subject has been exposed.

7. A method as claimed in claim 6 wherein the measure of the PBGS protein function of enzyme activity is based on formation of porphobilinogen (PBG) from delta-aminolevulinate (ALA) under the influence of said PBGS.

8. A method as claimed in claim 6 wherein said PBGS is reactivated by warming in the presence of Zinc (II) and a reducing agent.

9. A method as claimed in claim 7, wherein the formation of PBG is determined by forming uroporphyrinogen I from PBG and detecting the intensity of fluorescence of said uroporphyrinogen I.

10. A method as claimed in claim 1, wherein said measuring step is performed on immobilized PBGS.

11. A method as claimed in claim 6, wherein said measuring step is performed with said PBGS in the presence of an exogenous protein in an amount effective to potentiate inhibition of said PBGS by said lead.

12. A method as claimed in claim 11, wherein said exogenous protein is bovine serum albumin.

* * * * *